United States Patent
Meese

(10) Patent No.: US 7,982,058 B2
(45) Date of Patent: Jul. 19, 2011

(54) CHIRAL INTERMEDIATE, PROCESS FOR PRODUCING THE SAME AND ITS USE IN THE MANUFACTURE OF TOLTERODINE, FESOTERODINE, OR THE ACTIVE METABOLITE THEREOF

(75) Inventor: Claus Meese, Monheim (DE)

(73) Assignee: UCB Pharma GmbH, Monheim (DE)

( * ) Notice: Subject to any disclaimer, the term of this patent is extended or adjusted under 35 U.S.C. 154(b) by 57 days.

(21) Appl. No.: 12/304,323

(22) PCT Filed: Jun. 6, 2007

(86) PCT No.: PCT/EP2007/005008
§ 371 (c)(1),
(2), (4) Date: Dec. 11, 2008

(87) PCT Pub. No.: WO2007/144097
PCT Pub. Date: Dec. 21, 2007

(65) Prior Publication Data
US 2009/0192224 A1   Jul. 30, 2009

(30) Foreign Application Priority Data
Jun. 12, 2006  (EP) .................................... 06012052

(51) Int. Cl.
*C07D 311/00* (2006.01)
(52) U.S. Cl. ...................................................... 549/399
(58) Field of Classification Search .................. 549/399
See application file for complete search history.

(56) References Cited

U.S. PATENT DOCUMENTS

| 6,713,464 B1 | 3/2004 | Meese et al. |
| 6,858,650 B1 | 2/2005 | Meese |
| 2009/0306384 A1* | 12/2009 | Ahman et al. ............... 544/376 |

FOREIGN PATENT DOCUMENTS

| WO | 89/06644 | 7/1989 |
| WO | 94/11337 | 5/1994 |
| WO | 98/43942 | 10/1998 |
| WO | 01/49649 | 7/2001 |
| WO | 01/96279 | 12/2001 |

OTHER PUBLICATIONS

March's Advanced Organic Chemistry, 5th Ed., a Wiley-Interscience Publication, 2001, pp. 1514-1519.
Walker, "The Functional Group Selectivity of Complex Hydride Reducing Agents." Chem. Soc. Rev. 5, 1976, pp. 23-50.
Soai et al., "Mixed Solvents Containing Methanol as Useful Reaction Media for Unique Chemoselective Reductions Within Lithium Borohydride." J. Org. Chem. 51, 1986, pp. 4000-4005.

* cited by examiner

Primary Examiner — Nizal Chandrakumar
(74) Attorney, Agent, or Firm — Kenyon & Kenyon LLP

(57) ABSTRACT

The compound of formula (I): is provided. It may be produced by subjecting a compound of formula (IV) to a reduction reaction wherein R represents hydrogen, straight or branched $C_1$-$C_6$ alkyl. This compound is a valuable intermediate which may be used in the synthesis of fesoterodine, tolterodine, its active metabolite, and related compounds.

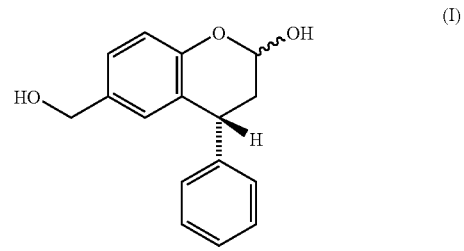

(I)

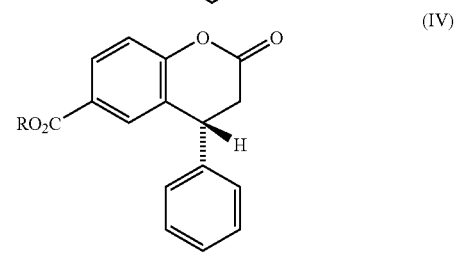

(IV)

9 Claims, No Drawings

CHIRAL INTERMEDIATE, PROCESS FOR PRODUCING THE SAME AND ITS USE IN THE MANUFACTURE OF TOLTERODINE, FESOTERODINE, OR THE ACTIVE METABOLITE THEREOF

CROSS REFERENCE TO RELATED APPLICATION

This application is a 371 of International Patent Application No. PCT/EP2007/005008, filed Jun. 6, 2007, which claims priority to European Patent Application No. 06012052.4, filed Jun. 12, 2006. The contents of these applications are hereby incorporated by reference in their entireties.

TECHNICAL FIELD

The present disclosure relates to a new chiral intermediate which is the compound represented by the following formula (I), and a method for producing the same.

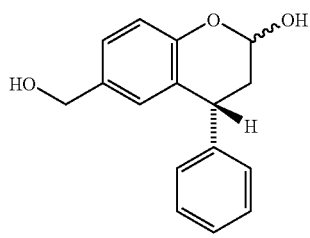
(I)

It also relates to a shortened process for the preparation of (R)-2-(3-diisopropylamino-1-phenylpropyl)-4-(hydroxymethyl)phenol which is known as the active metabolite (hereafter named the "active metabolite") of tolterodine and fesoterodine. The target compound has the following formula (II):

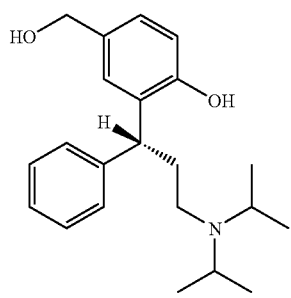
(II)

This process may also be employed in the synthesis of tolterodine or the phenolic monoesters of formula (III):

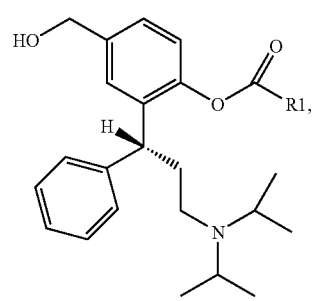
(III)

wherein R1 is hydrogen, a straight, branched or cyclic $C_1$-$C_6$ alkyl group or an aryl group which may optionally be substituted.

A particular preferred example of the phenolic monoesters of formula (III) is fesoterodine which is chemically defined as R-(+)-isobutyric acid 2-(3-diisopropylamino-1-phenylpropyl)-4-(hydroxymethyl)phenyl ester. It has the formula (IIIa) depicted below.

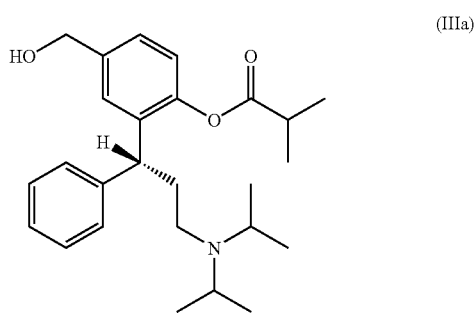
(IIIa)

Tolterodine, the active metabolite, and its phenolic monoesters of formula (III) including fesoterodine are known e.g. from WO 89/06644, WO 94/11337 and U.S. Pat. No. 6,713,464, respectively.

BACKGROUND

In man, normal urinary bladder contractions are mediated, (inter alia), through cholinergic muscarinic receptor stimulation. Muscarinic receptors not only mediate normal bladder contractions, but may also mediate the main part of the contractions in the overactive bladder resulting in symptoms such as urinary frequency, urgency and urge urinary incontinence.

After administration of fesoterodine and other phenolic monoesters of formula (III) to mammals, such as humans, these compounds are cleaved to form the active metabolite. The active metabolite is known to be a potent and competitive muscarinic receptor antagonist (WO 94/11337). Therefore, fesoterodine and other phenolic esters of formula (III) represent potential prodrugs for the active metabolite, and are drugs which are effective in the treatment of overactive bladder with symptoms of urge urinary incontinence, urgency, and urinary frequency, as well as detrusor hyperactivity (as described e.g. in U.S. Pat. No. 6,713,464). Tolterodine is another well known drug for the treatment of overactive bladder.

Two different routes for the synthesis of the phenolic monoesters of formula (III) such as fesoterodine have previously been described in U.S. Pat. No. 6,713,464 and WO 01/96279, respectively. WO 01/49649 discloses a certain method for producing tolterodine.

The synthesis of the active metabolite is also known in the prior art. WO 94/11337 and WO 98/43942 both describe a multi-stage process to synthesize the active metabolite.

However, all these prior art processes are inconvenient, because they comprise a large number of steps e.g. in accordance with the synthesis disclosed in WO 94/11337, 11 steps are necessary for obtaining the active metabolite. Similarly, 12 different reaction steps are necessary for producing the phenolic monoesters of formula (III) (see U.S. Pat. No. 6,713,464).

A first approach for shortening the synthesis of the phenolic monoesters of formula (III) is disclosed in WO 01/96279. In the process according to WO 01/96279, the preferred R-enantiomer of the compounds of formula (II) or (III) is obtained by utilizing the diastereomeric cinchonidine salt of (R,S)-4-phenyl-2-chromanone-6-carboxylic acid ((2b), Scheme 1). If this salt is crystallized, the R-enantiomer of 4-phenyl-2-chromanone-6-carboxylic acid predominates as the acid component (more than 95% ee.). By recrystallization, the enantiomeric purity can be increased up to 99% ee.

The optically pure lactone (step 3, (3)) is then liberated by acidification and subsequently converted into its methyl ester (4). The lactone (4) is then reduced with one molar equivalent of a hydride, thereby obtaining the lactol (5). The lactol intermediate (5) is then used to prepare the active metabolite (II) in 2 additional steps by first reductively aminating the lactol (5) and in a second step by the reduction of the ester substituent to give the benzylic hydroxyl function of the active metabolite (II), which can be then acylated to give a compound of formula (III).

Notwithstanding the significant reduction in the number of necessary operations as compared to previous routes, the synthesis of the active metabolite of formula (II) still requires 8 steps in total, and 5 steps from 4-phenyl-2-chromanone-6-carboxylic acid.

Owing to the large number of steps involved, all prior art processes are complex, and the overall yield of the active metabolite is unsatisfactory. As a consequence there was a need for a further shortening of the synthesis of the compounds of formula (II) or (III), whereby the above disadvantages may be avoided.

In WO 01/96279 the reduction of the lactone (4) was performed at mild conditions and with a stoichiometry [reducing agent/compound of formula (4)] of about 1:1 or less because of concerns that harsher reduction conditions would lead to an opening of the lactone ring. Based on the state of the art, it would have been expected that harsher reduction conditions would result in an over-reduction of the intermediate lactol such that both the lactone as well as the benzoate ester functions would be fully reduced thus leading to the synthetically unwanted primary alcohol depicted below (March's Organic Chemistry, $5^{th}$ Ed, Wiley Publication, 2001, see particularly tables 19-3 and 19-5; Walker, Chem Soc Rev 5, 1976, 23; see particularly Table 7; Soai et al, J Org Chem 51, 1986, 4000). Expected Reduction Reaction:

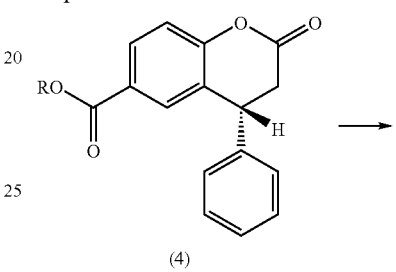

(4)

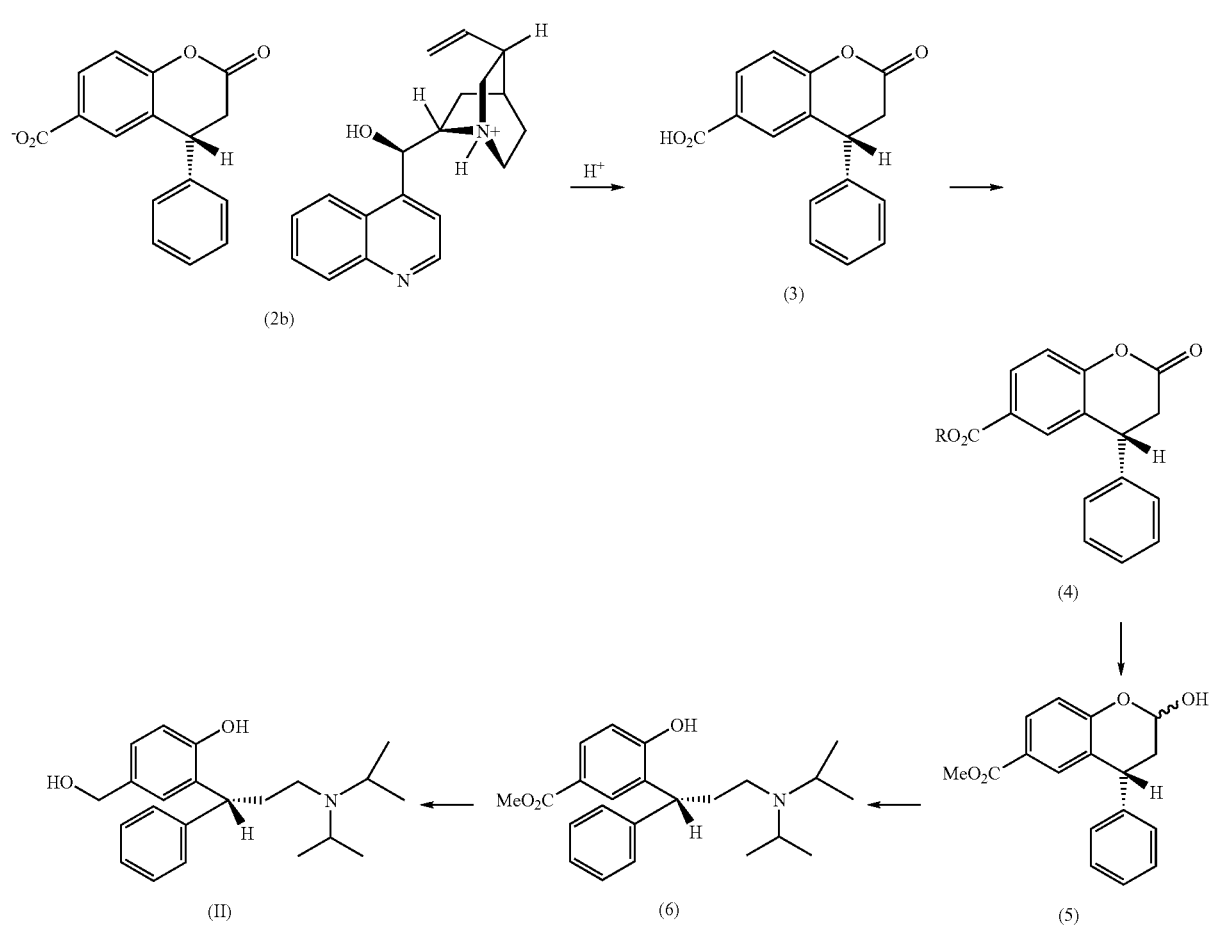

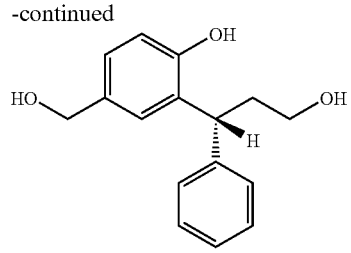

The problem was thus to achieve the reduction of the benzoate ester or benzoic acid function to the primary alcohol while at the same timing stopping the reduction of the lactonic ester at the aldehyde (lactol) stage, with the particular challenge that lactones are generally more susceptible to reduction than carboxylic acids or esters (see e.g. March's Organic Chemistry, 5$^{th}$ Ed, Wiley Publication, 2001, tables 19-3 and 19-5). Surprisingly, it has now been found that under appropriate conditions in fact the benzoate ester of compound (4) can be selectively reduced without reduction of the lactol. The resulting compound of formula (I) can then be converted in one step to the active metabolite of formula (II), thereby saving one step in the overall production process (scheme 2).

SUMMARY

The present disclosure provides the compound of formula (I):

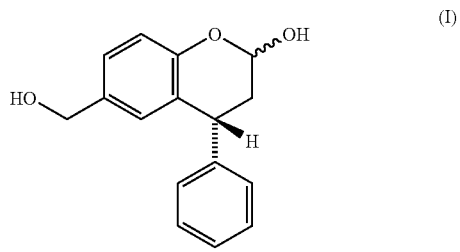

as well as a process for its production wherein a compound of formula (IV) is subjected to a chemo-selective reduction reaction:

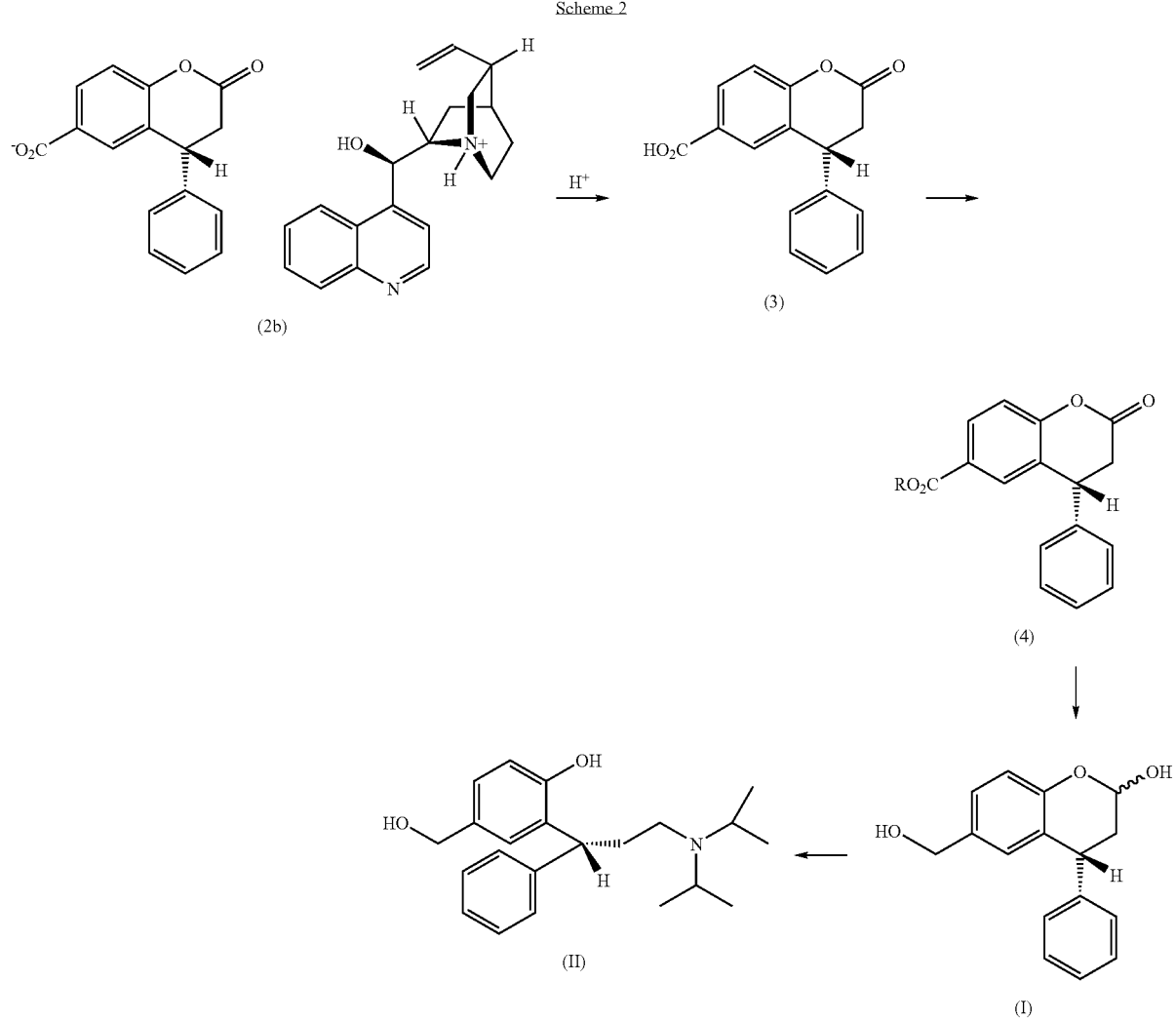

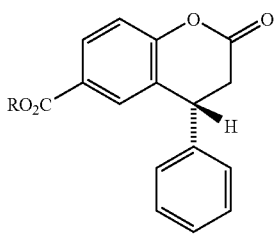

wherein R represents hydrogen or a straight or branched $C_1$-$C_6$-alkyl group, preferably methyl or isopropyl.

DETAILED DESCRIPTION

In the first aspect, the present disclosure relates to a compound of formula (I) and a method for producing the same:

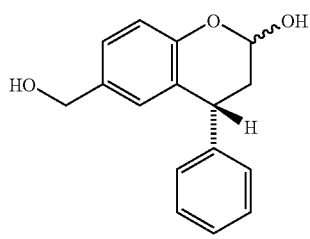

It is clear to the skilled person that the compound of formula (I) may also be present in the form of an open-chain 5-hydroxy aldehyde.

In the process of the present disclosure, the compound of formula (IV) is subjected to a reduction reaction, thereby obtaining the compound of formula (I).

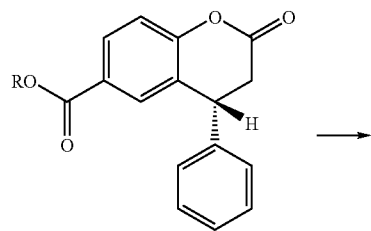

formula IV

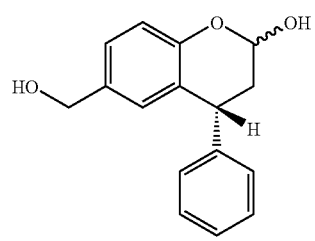

formula I

Preferably, the reduction is performed with the aid of a reducing agent in a molar ratio [reducing agent/compound of formula (IV)] of about 2 or more, and particularly preferably of about 3 or more.

If R in formula IV is a straight or branched $C_1$-$C_6$ alkyl group, aluminium hydrides, more preferably lithium tri-(tert.-butoxy)-aluminium hydride or dialkyl aluminium hydrides are used as reducing agents, and particularly preferably diisobutylaluminum hydride. In one specific embodiment of the present disclosure, diisobutylaluminum hydride is being used as reducing agent and the molar ratio of diisobutylaluminum hydride to the compound of formula (IV) is between 2 and 4, preferably between 2.5 and 3.5, and even more preferably the molar ratio is about 3.

If R in formula IV represents hydrogen, borane or diborane are preferably used. In those cases the molar equivalents of the reducing agent [compared to a compound of formula (IV)] referenced further above refer to the molar equivalents of available hydrides. For example, if BH3 will be used as hydrogenation agent, the molar ratio [BH3/compound of formula (IV)] may be about 1 or more, or about 1.5 or more, or sometimes even about 2 or more.

The reaction may be performed under conditions which may be appropriately determined by the skilled person.

In a particularly preferred embodiment, the reaction is carried out using the reducing agent such as the diisobutylaluminum hydride or the borane at a temperature of below about 0° C., preferably around −25° C. to 0° C. or around −20° C. to 0° C., particularly preferably at a temperature between about −25° C. and −5° C., or even more preferably between −20° C. and −10° C.

Conveniently, the reaction is carried out in a suitable solvent, such as an ether (e.g. THF) or, preferably, in an aromatic hydrocarbon (e.g. toluene).

According to one embodiment of the present disclosure, the reducing agent is added to a solution of a compound of formula (4) in toluene, preferably dropwise, at a temperature of about −5° C. to about −20° C.

The compound of formula (I) may be conveniently obtained in crystalline form, e.g. by crystallization from toluene, or by recrystallization from ethyl acetate or toluene as the solvent and, if necessary, hexane as the crystallization agent.

The compound of formula (IV) which is used as the starting material in the present disclosure, may be obtained as described in WO 01/96279.

In particular, 4-hydroxybenzoic acid or a lower alkyl ester thereof (PHB ester; para-hydroxybenzoate), preferably its methyl ester (1), is reacted with cinnamic acid to form a compound of the general formula (2).

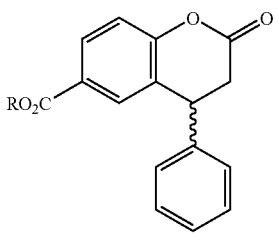

wherein R has the meaning of hydrogen, straight or branched $C_1$-$C_6$ alkyl, preferably methyl or isopropyl. By using a 4-hydroxybenzoate as the starting material, the free, crystalline acid represented by formula (2a) can be obtained.

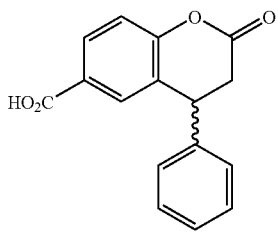

(2a)

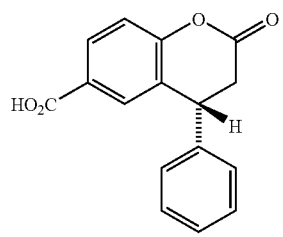

(3)

The reaction takes place at an elevated temperature in the presence of a catalyst. The preferred solvent is acetic acid. Suitable catalysts are protonic acids, such as sulfuric acid or hydrochloric acid. Conveniently, the reaction temperature is in the range of between 50° C. and 117° C., preferably 100° C. If the reaction is carried out under the conditions as mentioned above, the compound of formula (2a) may be obtained as a crystalline solid in a satisfactory yield and purity (yield: about 70-78%; purity >90%). If necessary, any remaining impurities may be removed by recrystallisation, using e.g. 2-butanone, acetic acid or N-methylpyrrolidin-2-one as the solvent.

The compound of formula (2a) forms crystalline acid addition salts with inorganic or organic bases. Chiral organic bases yield diastereomeric salts. In these diastereomeric salts one enantiomer of the compound of formula (2a) is contained in a significant enantiomeric excess. If the chiral tertiary amine cinchonidine is used in the formation of the diastereomeric salt, the crystalline salt according to formula 2b is obtained in 90% purity.

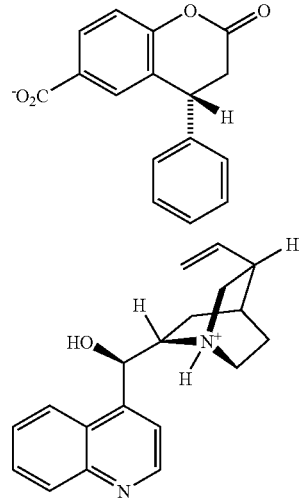

(2b)

The R-enantiomer of the acid component predominates in this crystalline form, and the enantiomeric excess may be as high as 95% or more. By further recrystallisation, the enantiomeric purity may be increased up to 99% ee.

The free acid of the compound of formula 3 may be isolated from an aqueous solution or suspension of the diastereomeric salt of formula (2b) by acidification and extraction with a suitable solvent. Ethyl acetate is preferably employed as the extracting agent.

The dextrorotatory compound of formula (3) is activated and converted to an ester of the general formula (4), in which R has the meaning of straight or branched $C_1$-$C_6$ alkyl, preferably methyl or isopropyl.

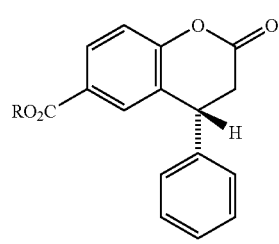

(4)

In another aspect, the present disclosure relates to the use of the compound of formula (I) in a shortened synthesis of tolterodine, the active metabolite of tolterodine having formula (II) and its phenolic monoesters having formula (III):

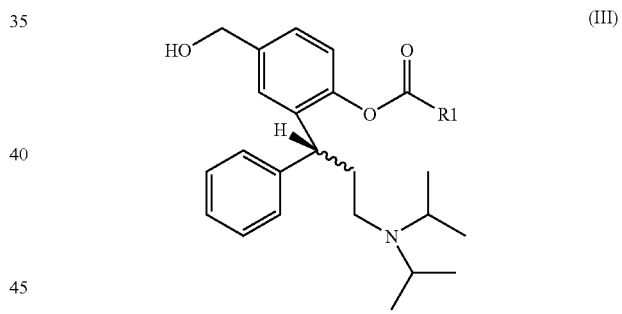

(III)

wherein R1 is hydrogen, a straight, branched or cyclic $C_1$-$C_6$ alkyl group or an aryl group. These alkyl or aryl groups may optionally be substituted. Preferred monoesters of formula (II) which may be produced using the process of the present disclosure are the ones disclosed in U.S. Pat. No. 6,713,464, such as:

(±)-formic acid 2-(3-diisopropylamino-1-phenylpropyl)-4-hydroxymethylphenyl ester,
(±)-acetic acid 2-(3-diisopropylamino-1-phenylpropyl)-4-hydroxymethylphenyl ester,
(±)-propionic acid 2-(3-diisopropylamino-1-phenylpropyl)-4-hydroxymethylphenyl ester,
(±)-n-butyric acid 2-(3-diisopropylamino-1-phenylpropyl)-4-hydroxymethylphenyl ester,
(±)-isobutyric acid 2-(3-diisopropylamino-1-phenylpropyl)-4-hydroxymethylphenyl ester,
R-(+)-isobutyric acid 2-(3-diisopropylamino-1-phenylpropyl)-4-hydroxymethylphenyl ester,
(±)-2,2-dimethylpropionic acid 2-(3-diisopropylamino-1-phenylpropyl)-4-hydroxymethylphenyl ester, (±)-2-acetamidoacetic acid 2-(3-diisopropylamino-1-phenylpropyl)-4-hydroxymethylphenyl ester,
(±)-cyclopentanecarboxylic acid 2-(3-diisopropylamino-1-phenylpropyl)-4-hydroxymethylphenyl ester,
(±)-cyclohexanecarboxylic acid 2-(3-diisopropylamino-1-phenylpropyl)-4-hydroxymethylphenyl ester,
(±)-benzoic acid 2-(3-diisopropylamino-1-phenylpropyl)-4-hydroxymethylphenyl ester,
R-(±)-benzoic acid 2-(3-diisopropylamino-1-phenylpropyl)-4-hydroxymethylphenyl ester,
(±)-4-methylbenzoic acid 2-(3-diisopropylamino-1-phenylpropyl)-4-hydroxymethylphenyl ester,
(±)-2-methylbenzoic acid 2-(3-diisopropylamino-1-phenylpropyl)-4-hydroxymethylphenyl ester,
(±)-2-acetoxybenzoic acid 2-(3-diisopropylamino-1-phenylpropyl)-4-hydroxymethylphenyl ester,
(±)-1-naphthoic acid 2-(3-diisopropylamino-1-phenylpropyl)-4-hydroxymethylphenyl ester,
(±)-2-naphthoic acid 2-(3-diisopropylamino-1-phenylpropyl)-4-hydroxymethylphenyl ester,
(±)-4-chlorobenzoic acid 2-(3-diisopropylamino-1-phenylpropyl)-4-hydroxymethylphenyl ester,
(±)-4-methoxybenzoic acid 2-(3-diisopropylamino-1-phenylpropyl)-4-hydroxymethylphenyl ester,
(±)-2-methoxybenzoic acid 2-(3-diisopropylamino-1-phenylpropyl)-4-hydroxymethylphenyl ester,
(±)-4-nitrobenzoic acid 2-(3-diisopropylamino-1-phenylpropyl)-4-hydroxymethylphenyl ester,
(±)-2-nitrobenzoic acid 2-(3-diisopropylamino-1-phenylpropyl)-4-hydroxymethylphenyl ester.

A particular preferred embodiment of the compound of formula (III) is fesoterodine or its salts, especially its hydrogen fumarate or its hydrochloride hydrate. In this preferred embodiment, R in formula (III) represents an isopropyl group.

In the shortened synthesis according to the present disclosure, the compound of formula (IV) is reduced to obtain the compound of formula (I) which can be subsequently converted to tolterodine, the active metabolite of tolterodine, or the phenolic monoesters of formula (III), respectively, as follows.

The compound of formula (I) is suitable for reductive amination, and can thus be used for the production of the active metabolite (formula II), which can then be further processed to the corresponding phenolic monoesters of formula (III).

The compounds of formula (II) can be produced from the compound of formula (I) as described in WO 01/96279: Briefly, it will be processed by reductive amination with primary or, preferably, secondary amines such as isopropyl amine or N,N-diisopropyl amine, respectively. The reductive amination may be conducted under conditions which are similar to the prior art processes (see e.g. U.S. Pat. No. 6,713,464; WO 01/96279) and may be suitably chosen by the skilled person. In particular, the reductive amination may be performed in the presence of a hydrogen transfer donor such as formic acid or, preferably, hydrogen gas, and a suitable catalyst, such as e.g. a noble metal catalyst. A preferred catalyst is palladium, particularly Pd/C. This process is further exemplified in the experimental part of this application.

The compounds of formula (II) can then be acylated to obtain the phenolic monoesters of the general formula (III), such as, specifically, fesoterodine. Examples of this acylation are described e.g. in U.S. Pat. No. 6,713,464 and U.S. Pat. No. 6,858,650. Specifically, Fesoterodine may be produced from the compound of formula (II) as follows:

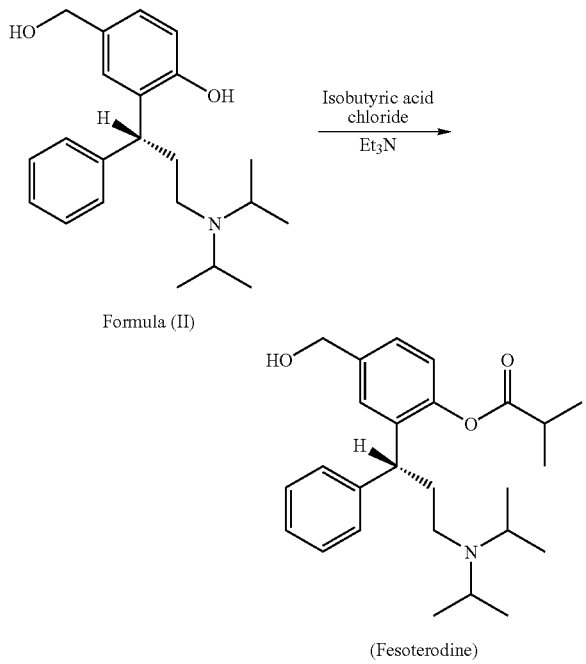

Formula (II)

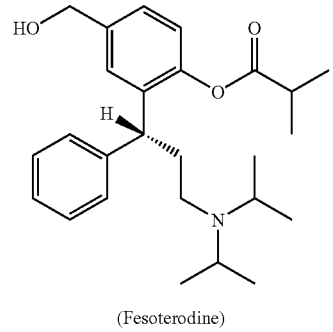

(Fesoterodine)

The formation of other phenolic monoesters of the Active Metabolite is possible by using other organic acid halides in the above scheme.

The compounds of formula (III), e.g. Fesoterodine may then be used to form suitable salts, such as the hydrogen fumarate salt as depicted below

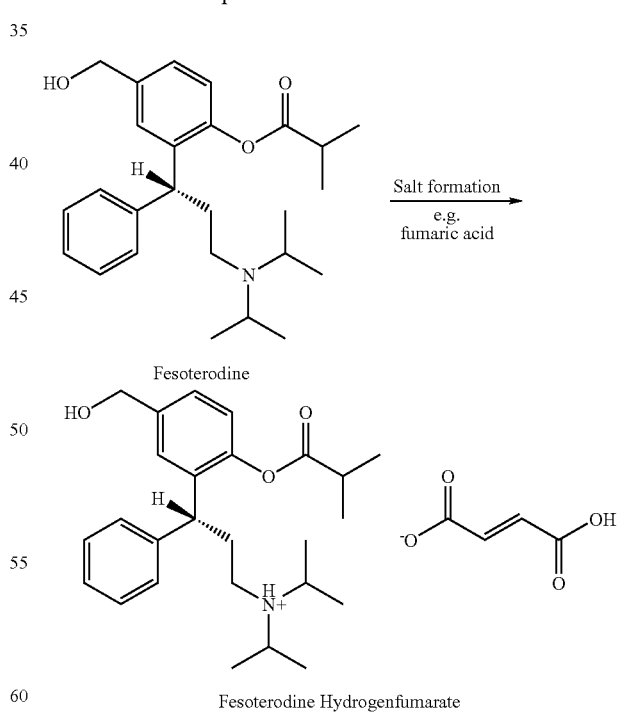

Fesoterodine

Fesoterodine Hydrogenfumarate

The compound (III) (phenolic monoesters of the Active Metabolite including Fesoterodine or pharmaceutically acceptable salts thereof) can then be formulated in a known manner to obtain an oral, parenteral, or transdermal medicament.

The Active Metabolite of formula (II) can also be transformed into tolterodine by reductive deoxygenation. After acylation of the Active Metabolite using acetyl chloride, the resulting diester can be reductively deoxygenated using hydrogen gas and acetic acid in the presence of Pd/C, followed by treatment with an aqueous alkaline solution.

Of course, the intermediate of formula (I) provided by the present disclosure may also be used in the synthesis of other chiral chemicals.

The present disclosure will now be explained in more detail by reference to the following examples which are not intended to limit the scope of the present disclosure.

REFERENCE EXAMPLES cf. WO 01/96279

NMR Spectroscopy

All compounds described were characterised by $^1$H and/or $^{13}$C NMR spectroscopy (Instrument: Bruker DPX 200). The chemical shifts are indicated for the $^{13}$C NMR spectra (50 MHz, ppm values) based on the solvents CDCl$_3$ (77.10 ppm), CD$_3$OD (49.00 ppm) or hexadeuteriodimethyl sulfoxide (DMSO-d$_6$, 39.70 ppm) as internal standards. $^1$H NMR data (200 MHz, ppm) are based on tetramethylsilane as an internal standard (0.00 ppm).

Determination of the Enantiomeric Purity
a) HPLC:

The separations were performed on a column from Daicel (Chiralpak AD, 250×4.6 mm), the eluent was n-heptane/ethanol/trifluoroacetic acid (92.5/7.5/0.1% v/v), the flow rate was 1 ml/min, and detection was by UV-spectroscopy (250 nm). Typical retention times, e.g. for the enantiomers of (3), were found to be 18.0 and 19.5 min.

b) Capillary Electrophoresis (CE):

The separations were performed in a Beckman-Coulter model MDQ device in 60 cm (ID: 75 pm) capillaries, with a field of 500 V/cm in a buffer of 100 mM/100 nM tris-buffer/boric acid, pH 8.5, in the presence of 3% w/v hydroxypropyl-β-cyclodextrin modifier. The detection is performed using UV-spectroscopy at 200 nm. Typical retention times of the enantiomers, e.g. the diacides formed by alkaline hydrolysis of the enantiomers of (3), are 6.6 and 6.8 minutes.

Further Methods for Analysis

The optical rotations were determined at 589.3 nm and ambient temperature using a Perkin Elmer type 241 polarimeter.

The melting points (Mp) described are indicated as uncorrected values and were recorded using a Mettler FP 1 instrument, and sometimes also by differential thermal analysis (DSC).

IR spectra were recorded on a Perkin-Elmer FTIR 1610 series spectrometer with a resolution of 4 cm$^{-1}$.

Gas chromatographic mass spectroscopy (GC-MS): the spectra (mass/charge ratios and relative intensity (%)) were recorded on a Finnigan TSQ 700 Triole Mass Spectrometer in the positive (P-Cl) or negative (N-Cl) chemical ionisation mode using methane or ammonia as reactant gas. Hydroxyl compounds were analysed as trimethylsilyl ether derivatives.

Coupled liquid chromatography-mass spectrometry (LC-MS): Waters Integrity System, Thermabeam Mass Detector (EI, 70 eV), mass/charge ratios and relative intensity are reported.

Elemental analyses were prepared by Pascher.

1. (R,S)-4-Phenyl-2-chromanone-6-carboxylic Acid (Formula 2a)

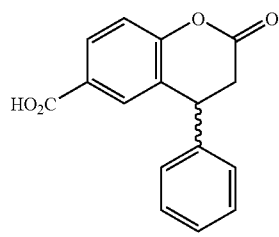

A mixture of cinnamic acid (100 g, 0.68 mol), methyl 4-hydroxybenzoate (108 g, 0.71 mol) and acetic acid (80 ml) is heated to 100° C. 80 ml of 96% sulfuric acid are added to the resulting clear solution, while stirring. After 2 hours, crystal begin to form. Stirring is continued at the same temperature for 16 hours, the mixture is cooled to ambient temperature and diluted with 500 ml water. The precipitated crystals are separated by filtration, washed with diethyl ether and dried in vacuo.

Crude product: 142 g (yield 78% of theory), pale beige crystals.

Mp 246° C.

$^1$H-NMR (DMSO-d$_6$): 3.18 (d, 2H, J=6.6 Hz, CH$_2$), 4.62 (t, 1H, J=6.6 Hz, CH), 7.14-7.43 (m, 6H), 7.62 (s, 1H), 7.90 (d, 1H, J=8.6 Hz).

$^{13}$C-NMR (DMSO-d$_6$): 35.93, 39.26, 117.20, 126.81, 127.13, 127.65, 127.70, 129.24, 129.95, 130.25, 140.91, 154.80, 166.66, 167.30

Evidence for Structure Determination:

Titration with aqueous 0.1 N NaOH in dioxane/water against phenolphthalein gives one equivalent carboxylic acid/mol. In capillary electrophoresis, the electropherogram displays one main peak (>90%) for a singly charged anion. After the alkaline hydrolysis this peak disappeared, and a new peak having the same intensity appeared with a retention time corresponding to a dianion. An excess of triethylamine is added to a methanolic solution of the acid, and the reaction mixture is allowed to stand at ambient temperature for several days. Using thin layer chromatography, it is confirmed that the educt was converted. The product exhibits a mono methyl ester resonance in the NMR spectra, indicating the formation of (R,S)-4-hydroxy-3-(2-methoxy-carboxyl-1-phenylethyl)-benzoic acid.

Thus, (R,S)-2a is the monobasic acid lactone and not the open-chain phenolic diacid.

2. (R)-4-Phenyl-2-chromanone-6-carboxylic Acid Cinchonidine Salt (Formula 2b)

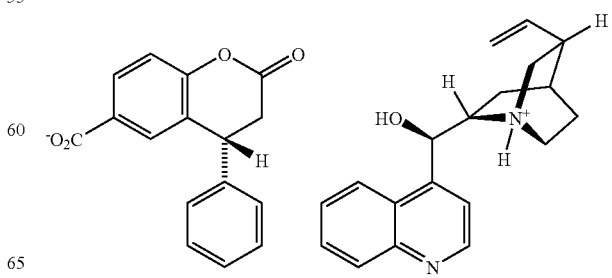

(R,S)-4-Phenyl-2-chromanone-6-carboxylic acid (2.28 g, 8.5 mmol) and 2.36 g (8 mmol) of cinchonidine are dissolved in 40 ml of boiling 2-butanone. The solution is stirred at ambient temperature for 18 hours and the precipitated crystals are filtered off and dried in vacuo.

Yield: 2.13 g of pale yellow crystals of the cinchonidine salt of (R)-4-phenyl-2-chromanone-6-carboxylic acid (90% of theory, 90% ee. (HPLC)). Recrystallisation from the same solvent yields a crystalline salt with 99.3% ee.

Mp: 197.5° C.

$^{13}$C-NMR (CDCl$_3$/CD$_3$OD): 18.17, 24.39, 26.90, 36.86, 37.21, 40.53, 43.32, 54.12, 60.03, 66.23, 116.51, 118.60, 122.70, 124.73, 127.29, 127.41, 128.07, 129.01, 129.31, 129.78, 130.09, 133.02, 137.70, 140.35, 147.20, 149.57, 153.37, 167.64, 172.87.

$[\alpha]_D^{20}$=−38.7 (c=1.0, MeOH).

3. (R)-4-Phenyl-2-chromanone-6-carboxylic Acid (Formula 3)

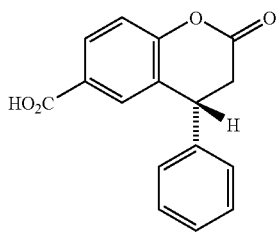

An excess of aqueous hydrochloric acid is added to a stirred suspension of the salt of formula (2) in ethyl acetate at ambient temperature. After one hour the organic phase is separated, washed with water and dried over sodium sulfate. After filtration, it is evaporated to dryness, and the crystalline residue is recrystallised from 2-butanone/cyclohexane. Colourless crystals are obtained in an almost quantitative yield (99.2% ee.).

Mp 224.9° C.

$^{13}$C-NMR (CDCl$_3$/CD$_3$OD): 36.43, 40.19, 116.92, 125.54, 126.96, 127.10, 127.57, 128.98, 130.29, 130.59, 139.64, 154.71, 167.28, 167.50.

$[\alpha]_D^{20}$=+45.7 (c=1.0, MeOH).

4. (R,S)-2-Oxo-4-phenylchroman-6-carboxylic Acid Methyl Ester (Formula 4)

a) Four drops of pyridine and 17.7 ml (0.24 mol) of thionyl chloride are added to a mixture of (R)-4-Phenyl-2-chromanone-6-carboxylic acid (21.5 g, 0.08 mol) in 80 ml of toluene. After stirring for 30 min at ambient temperature, the mixture is heated to 90-100° C. for 2 hours, cooled and evaporated to dryness in a rotary evaporator. The oily residue is taken up in toluene and evaporated in vacuo. (R)-4-Phenyl-2-chromanone-6-carbonyl chloride is obtained as a pale yellow oil in a quantitative yield.

b) 3 g (0.094 mol) of methanol and 16 ml (0.12 mol) of triethylamine in 20 ml of THF are added to a solution of R-4-Phenyl-2-chromanone-6-carbonyl chloride (22.9 g, 0.08 mol) in absolute tetrahydrofuran (100 ml) at 0° C., while stirring. After stirring for 18 hours at ambient temperature, the mixture is filtered, and the filtrate is evaporated to dryness. After recrystallisation from boiling diethyl ester, 13.7 g (65% of theory) of (R)-2-oxo-4-phenylchroman-6-carboxylic acid methyl ester in the form of colourless crystals are obtained.

Example 1

(R)-6-Hydroxymethyl-4-phenylchroman-2-(R,S)-ol (Formula I)

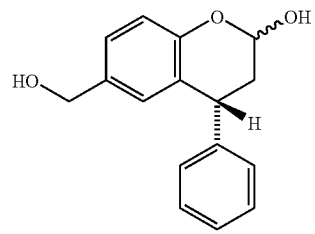

A solution of 1.5 M diisobutylaluminum hydride (100 ml, 150 mmol) in toluene is added dropwise to a cooled (temperature below −10° C.) solution of (R)-2-oxo-4-phenylchroman-6-carboxylic acid methyl ester (4) (14.11 g, 50.0 mmol) in 200 ml of dry toluene under stirring. The agitated mixture was allowed to stand for 2 hours at a temperature of −20° C. Subsequently, it was quenched with methanol, and water. The inorganic precipitate was removed by filtration, and the liquid phase was extracted several times with toluene. The combined organic phases were dried over sodium sulfate, filtered, and evaporated to dryness, thereby obtaining a pale yellow oil which solidified gradually.

Yield: 8.28 g (64.6%).

Melting point: 106.5° C.

Thin-layer chromatography (silica gel, solvent mixture EtOAc:n-heptane, 1:1/vol.-%):

Starting material (compound of formula IV) $R_f$: 0.71.

Product (compound of formula I) $R_f$: 0.37.

$^1$H NMR (CDCl$_3$, characteristic peaks): 4.4 ppm (s, 2H, HO—CH$_2$—), 5.4/5.6 ppm (d/s, ratio 1:4, O—CH—OH).

$^{13}$C NMR (CDCl$_3$, characteristic peaks): 64.77/65.13 ppm (ratio 4:1, HO—CH$_2$), 91.27/94.43 (ratio 4:1, O—CH—OH).

MS (PI, API, m/z): 239 [M+H—H$_2$O]$^+$. MW 256.30, C$_{16}$H$_{16}$O$_3$.

Example 2

(R)-4-Hydroxymethyl-2-(3-diisopropylamino-1-phenylpropyl)-phenol

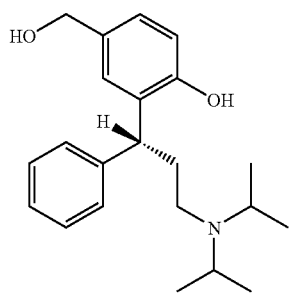

A mixture consisting of methanol, Pd/C catalyst, (R)-6-hydroxymethyl-4-phenylchroman-2-(R)-ol, and an excess of diisopropyl amine will be hydrogenated at ambient temperature at a pressure of 4 bar. After at least 18 hours, the reaction mixture will be filtered and evaporated to dryness. Subsequently, it is treated with 1 molar equivalent of a solution of lithium aluminium hydride in tetrahydrofuran for cleaving any cyclic hemiaminal. The reaction is quenched with water, and the product will be extracted with ethyl acetate. Removal of the solvent and drying in vacuum provides (R)-4-hydroxymethyl-2-(3-diisopropylamino-1-phenylpropyl)-phenol in the form of a colourless oil.

The invention claimed is:

1. A compound that is the essentially pure 4R-diastereomer of formula (I):

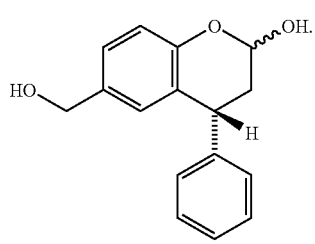

(I)

2. The compound of claim 1 in crystalline form.

3. A process for producing a compound of formula (I)

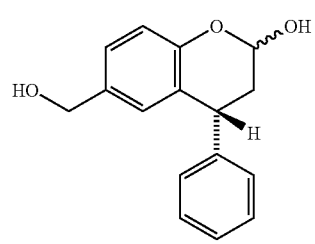

(I)

wherein a compound of formula (IV)

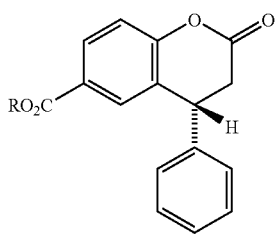

(IV)

is subjected to a reduction reaction;

wherein R represents hydrogen or a straight or branched $C_1$-$C_6$ alkyl group wherein the reducing agent is a dialkylaluminum hydride, and the reduction is performed with a reducing agent in a molar ratio [reducing agent/compound of formula (IV)] of about 3 or more.

4. The process of claim 3, wherein the reducing agent is a diisobutylaluminum hydride.

5. The process of claim 3, wherein the reducing agent is diisobutylaluminum hydride and the reaction is conducted at a temperature of −20° C. to 0° C.

6. The process of claim 5, wherein the reaction is conducted at a temperature of −20° C. to −5° C.

7. A process for producing the active metabolite of tolterodine or phenolic monoesters of formula (III):

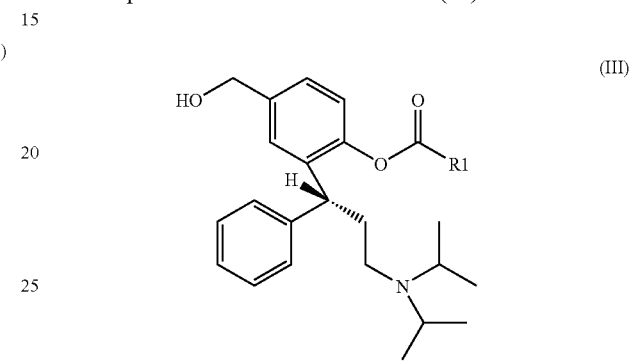

(III)

wherein R1 is selected from the group consisting of hydrogen, an optionally substituted straight, branched or cyclic $C_1$-$C_6$ alkyl group and an optionally substituted aryl group, or a salt thereof, comprising converting the essentially pure 4R-diastereomer of the compound of formula I

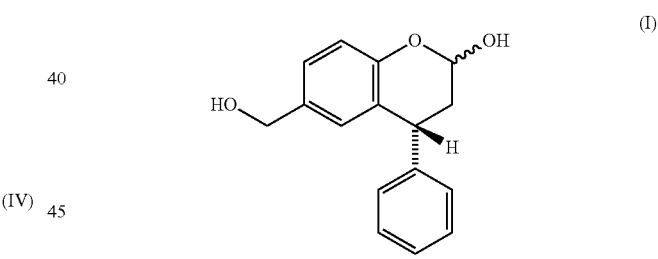

(I)

into the active metabolite of tolterodine or the phenolic monoesters of formula (III).

8. The process of claim 7, wherein fesoterodine or its salts is produced.

9. The process of claim 7, wherein fesoterodine hydrogen fumarate is produced.

* * * * *